United States Patent
Dalko et al.

(10) Patent No.: US 6,333,414 B1
(45) Date of Patent: Dec. 25, 2001

(54) PROCESS FOR THE SYNTHESIS OF TRISUBSTITUTED OXAZOLES

(75) Inventors: Maria Dalko, Gif S/Yvette; Jacqueline Dumats, Villepinte, both of (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/696,226

(22) Filed: Oct. 26, 2000

(30) Foreign Application Priority Data

Oct. 27, 1999 (FR) .................................................. 99 13446

(51) Int. Cl.[7] .................................................. C07D 263/32
(52) U.S. Cl. ........................................ 546/271.4; 548/235
(58) Field of Search ............................ 548/235; 514/374, 514/340; 546/269.4, 271.4

(56) References Cited

U.S. PATENT DOCUMENTS

| | | | | |
|---|---|---|---|---|
| 4,632,930 | * | 12/1986 | Carini et al. | 514/365 |
| 5,380,738 | * | 1/1995 | Norman et al. | 514/374 |
| 5,403,852 | * | 4/1995 | Barreau et al. | 514/374 |
| 5,719,163 | | 2/1998 | Norman et al. | 514/311 |
| 6,090,834 | * | 7/2000 | Talley et al. | 514/374 |

FOREIGN PATENT DOCUMENTS 1 206 403    9/1970  (GB) .

OTHER PUBLICATIONS

A.E. Siegrist, "Über eine neue Synthese zur Darstellung heterocyclisch substituierter Stilbenverbindungen, die Anil--Synthese", Helvetica Chimica Acta, vol. 50, No. 3, Apr. 20, 1967, pp. 906–957.

George McCoy et al., "Ortho Condensations which Lead to Oxazole or Imidazole Formation", Journal of the American Chemical Society, vol. 65, No. 11, Nov. 1943, pp. 2159–2162.

Rolf H. Prager et al., "Chemistry of 5–oxodihydroisoxazoles. Part 18. Synthesis of oxazoles by the photolysis and pyrolysis of 2–acryl–5–oxo–2,5–dihydroisoxazoles", Journal of the Chemical Society, Perkin Transactions, No. 17, Sep. 1997, pp. 2449–2672.

Jacqueline Collin et al., "Synthesis of α–Ketols Mediated by Divalent Samarium Compounds", Journal of Organic Chemistry, vol. 56, No. 9, Apr. 26, 1991, pp. 3118–3122.

* cited by examiner

*Primary Examiner*—Floyd D. Higel
*Assistant Examiner*—Kamal Saeed
(74) *Attorney, Agent, or Firm*—Finnegan, Henderson, Farabow, Garrett & Dunner, L.L.P.

(57) ABSTRACT

A process for the preparation of oxazoles of formula (II):

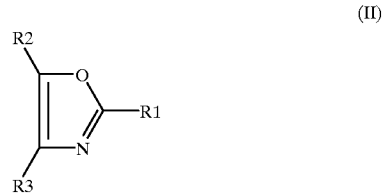

by reaction of thiourea with the corresponding diketone ester.

25 Claims, No Drawings

PROCESS FOR THE SYNTHESIS OF TRISUBSTITUTED OXAZOLES

The present invention relates to a novel process for the synthesis of oxazoles, in particular trisubstituted oxazoles. Oxazoles are known to be useful for the treatment of inflammation and inflammation-related disorders.

Oxazoles are well known in the literature, which describes several possible routes for the synthesis thereof.

Oxazles can be prepared by reaction of a diazide with a cyano derivative, in the presence of tungsten as a catalyst. See, for example, Tetrahedron Letters, 1974, 16, 1531, the disclosure of which is specifically incorporated by reference. This process can be illustrated by the following scheme:

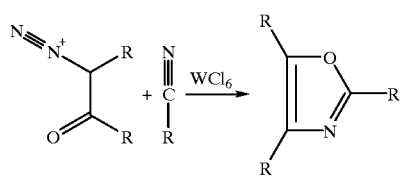

Trisubstituted oxazoles can also be prepared by using a primary amine as cyclization reactant. See, for example, J.A.C.S., 1943, 65, 2159, the disclosure of which is specifically incorporated by reference. This process can be illustrated by the following scheme:

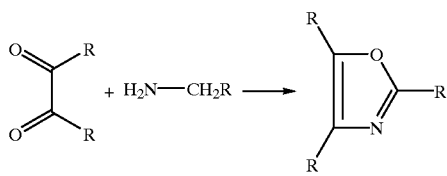

However, the synthesis of trisubstituted oxazoles according to either of these processes can be limited by the starting compound, and some starting materials can be either unavailable commercially or very difficult to synthesize. Consequently, depending on the nature of the substituents, some trisubstituted oxazoles cannot be prepared by either of these processes.

Trisubstituted oxazoles have also been prepared by the thermolysis and photolysis of an acylisoxazolone derivative. See, for example, J. Chem. Soc. Perkin, 1997, 2665, the disclosure of which is specifically incorporated by reference. This process can be illustrated by the following scheme:

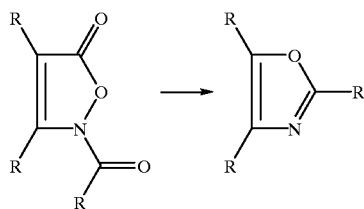

However, this process can require highly specialized equipment, for example to realize the photolysis of the starting materials. Therefore, the process may not easily be carried out industrially.

It is also known, by U.S. Pat. No. 5,719,163, the disclosure at which is specifically incorporated by reference, to synthesize certain trisubstituted oxazoles by using ammonium acetate in acetic acid at reflux, according to the following scheme:

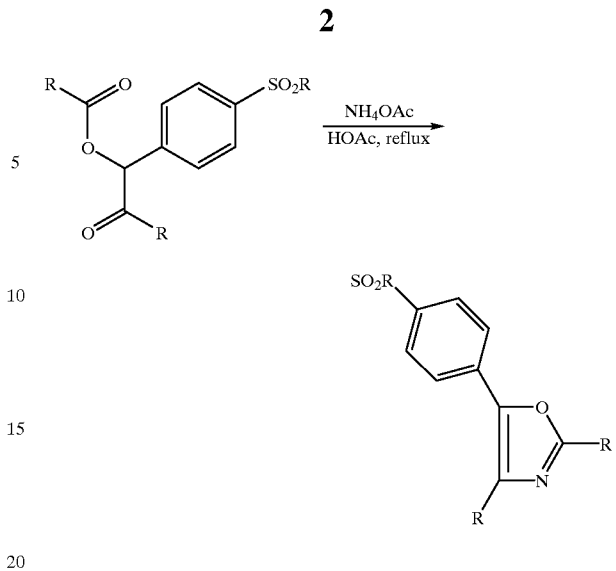

However, this process can exhibit the disadvantage of being carried out in the presence of acetic acid and thus in an acid medium.

An aim of the present invention is to provide a novel process for preparation of trisubstituted oxazoles which can be carried out from starting materials which are relatively easy to synthesize or already commercially available, and/or which does not require highly specialized equipment and/or which can be carried out under reaction conditions, particularly with respect to pH, which are industrially more favorable.

A subject-matter of the present invention is thus a process for the preparing a trisubstituted oxazole of formula (II):

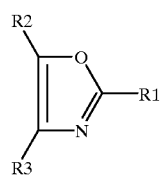

(II)

by reaction of thiourea with a diketone ester of formula (I):

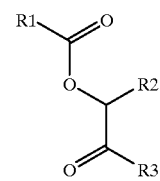

(I)

in which the $R_1$, $R_2$ and $R_3$ radicals, which may be identical or different, have the meanings given below.

It has been found that the process according to the invention can be carried out at a basic pH value, and even at a pH value close to neutral. Furthermore, the starting materials can be relatively easy to synthesize and this process can be carried out industrially and relatively inexpensively. Moreover, the reaction typically only comprises a single stage, which therefore can also facilitate its implementation on an industrial scale. Finally, it is possible, by virtue of this process, to prepare a large variety of trisubstituted oxazoles.

The present invention thus relates to a novel process for the preparation of an oxazole, including a trisubstituted oxazole, by reaction of thiourea with the diketone ester according to the following reaction scheme:

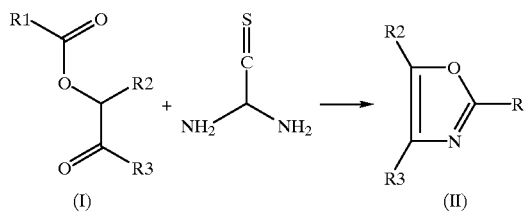

In the above reaction scheme, the $R_1$, $R_2$ and $R_3$ radicals, which are identical or different, are chosen from:

saturated and unsaturated, linear and branched $C_1$–$C_{12}$ hydrocarbon groups optionally substituted by at least one substituent chosen from —OR, —SR, —NRR', —COOR, —CN, —SO$_n$CH$_3$, —CF$_3$, and halogens, wherein the halogens are, for example, chosen from chlorine and fluorine, n has a value chosen from 0, 1, and 2, and wherein R and R', which are identical or different, are each chosen from hydrogen atoms and saturated and unsaturated, linear, branched, and cyclic $C_1$–$C_{12}$ hydrocarbons, such as, for example, alkyl, aryl, aralkyl, and alkylaryl groups;

aryl groups optionally substituted by at least one substituent chosen from saturated and unsaturated, linear and branched $C_1$–$C_{12}$ hydrocarbon groups, —OR, —NRR', —COOR, —CN, —SO$_n$CH$_3$, —SR, —CF$_3$ and halogens, such as chlorine and fluorine, and wherein R, R' and n have the same meanings as above; and saturated and unsaturated $C_{5-10}$ heterocyclic groups comprising at least one heteroatom chosen from N, S, and O, which are optionally substituted by at least one substituent chosen from linear and branched $C_1$–$C_{12}$ hydrocarbon groups, —OR, —NRR', —COOR, —CN, —SO$_n$CH$_3$, —SR, —CF$_3$ and halogens, such as chlorine and fluorine, and R, R' and n have the same meanings as above.

The $R_1$, $R_2$ and $R_3$ groups, which may be identical or different, also may each be chosen from:

saturated, linear and branched $C_1$–$C_6$ hydrocarbon groups, such as methyl, ethyl, propyl, n-butyl, isobutyl, and tert-butyl groups;

saturated, linear and branched $C_2$–$C_6$ hydrocarbon groups, substituted by at least one —OR group where R is chosen from phenyl and alkylaryl groups, such as —(CH$_2$)$_n$-phenyl groups, where n has a value ranging from 1 to 4, such as from 1 and 2;

phenyl groups;

phenyl groups substituted by at least one group chosen from saturated $C_1$–$C_4$ hydrocarbon groups, such as methyl, ethyl, propyl, n-butyl, isobutyl, and tert-butyl groups;

phenyl groups substituted by at least one group chosen from —NRR' groups, wherein R and R', which can be identical or different, are each chosen from saturated $C_1$–$C_4$ hydrocarbon groups, such as methyl, ethyl, propyl, n-butyl, isobutyl, and tert-butyl groups;

phenyl groups substituted by at least one halogen, such as fluorine; and unsaturated $C_{5-6}$ heterocyclic groups comprising a ring having at least one nitrogen atom in the ring.

The reaction can be carried out in a dipolar aprotic solvent, such as dipolar aprotic solvents having a boiling point of greater than 130° C., such as greater than 140° C. and further such as greater than 160° C. The reaction can be carried out, for example, in DMF (dimethylformamide).

The reaction can be carried out at a temperature of at least 130° C., such as greater than 140° C. and further such as greater than 160° C. The reaction can be carried out at the reflux temperature of the solvent.

The reaction can also be carried out in the absence of a solvent, for example, under vacuum, at a temperature close to or greater than the melting point of at least one of the two reactants.

In one exemplary, but non-limiting, embodiment the process of the present invention can be carried out as follows:

the diketone ester (I) and thiourea are dissolved in the solvent, any useful amounts and ratios of reactants may be used, such as approximately 2 equivalents of thiourea per 1 equivalent of diketone ester; and the mixture is heated at a temperature of at least 130° C. for the time needed to bring the reaction to completion, which can be of the order of 5 to 10 hours.

The desired product, i.e., the oxazole of formula (II), can subsequently be isolated by an isolation method, such as an isolation method chosen from at least one of precipitation, filtration, and extraction.

Finally, the desired product can be subjected to at least one step chosen from washing, drying, recrystallizing, and purifying according to the usual methods, as needed or desired.

The desired product is generally obtained with a good yield.

Embodiments of the invention are illustrated in the following examples.

EXAMPLE 1

Preparation of 2,4,5-triphenyloxazole
Reaction Scheme

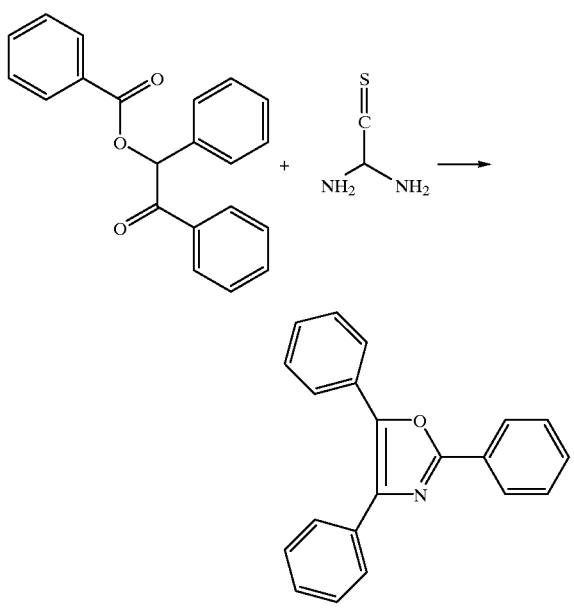

1 g of desyl benzoate and 0.5 g of thiourea (2 eq.) are added to 10 ml of dimethylformamide in a reactor. The solution is left stirring at 160° C. for 7 hours.

The solution is poured onto a water/ice mixture. The precipitated product is washed with water, filtered on a sintered glass filter under vacuum and placed overnight in a desiccator with $P_2O_5$.

Purification is carried out on silica gel (elutent: dichloromethane) and 0.62 g of a white powder is obtained (yield 68%).

$^1$H NMR spectrum (200 MHz; $CDCl_3$).

| δ (ppm) | splitting pattern | integration |
|---|---|---|
| from 7.27 to 7.35 | m | 6 |
| 7.39 | m | 3 |
| 7.61 | m | 4 |
| 8.05 | m | 2 |

EXAMPLE 2

Preparation of 2-methyl-4,5-diphenyloxazole
Reaction Scheme

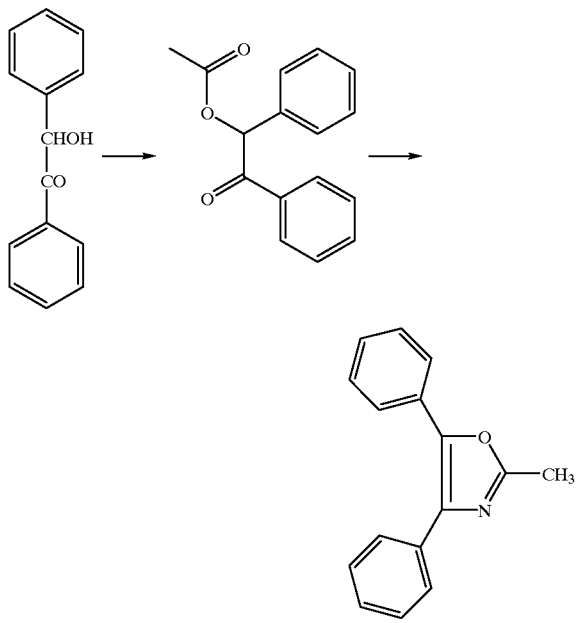

a) Synthesis of 2-oxo-1,2-diphenylethyl acetate 2 g of benzoin with 15 ml of acetic anhydride and a few drops of sulphuric acid are added to a reactor with stirring and at room temperature (25° C.) for 15 hours. Water and dichloromethane are added to the reaction mixture. The organic phase is recovered after separating by settling, dried over sodium sulphate, filtered and then concentrated to dryness under vacuum.

2.10 g of a white powder are obtained (yield: 88%).
Synthesis of 2-methyl-4,5-diphenyloxazole 0.2 g of the above 2-oxo-1,2-diphenylethyl acetate is dissolved in 10 ml of dimethylformamide in a reactor. 0.12 g of thiourea (2 eq.) is subsequently added and the reaction mixture is left to react at reflux (160° C.) for 10 hours. The reaction mixture is extracted using dichloromethane and then washed with water 3 times. The organic phase is recovered after separating by settling, dried over sodium sulphate, filtered and then concentrated to dryness under vacuum. The oil obtained is subsequently purified on a column of silica gel (elutent: dichloromethane).

0.13 g of an oil is obtained (yield: 54%).
$^1$H NMR spectrum (200 MHz; $d_6$-DMSO).

| δ (ppm) | splitting pattern | integration |
|---|---|---|
| 2.5 | s | 3 |
| 7.38 | m | 6 |
| 7.53 | m | 4 |

EXAMPLE 3

Preparation of [4-(2,5-diphenyloxazol-4-yl)phenyl] dimethylamine

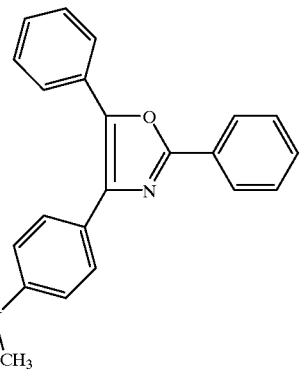

a) Benzoylation: preparation of 2-[4-(dimethylamino) phenyl]-2-oxo-1-phenylethyl benzoate 1 g of dimethylaminobenzoin with 0.6 g of triethylamine (1.5 eq.) and 0.1 g of dimethylaminopyridine are added to 20 ml of dichloromethane in a reactor with stirring at 0° C.

0.825 g of benzoyl chloride, in solution in 5 ml of dichloromethane, is gradually introduced therein using a dropping funnel (the introduction time having a duration of approximately 10 minutes). The reaction mixture is left to react for 5 hours. The reaction mixture is first washed with water and then twice with a basic aqueous solution (1N sodium hydroxide).

The organic phase is recovered after separating by settling, dried over sodium sulphate, filtered and then concentrated to dryness under vacuum.

1.2 g of a slightly yellow powder are obtained (yield: 86%).

b) Cyclization: synthesis of [4-(2,5-diphenyloxazol-4-yl] phenylldimethylamine 0.5 g of 2-[4-(dimethylamino)phenyl]-2-oxo-1-phenylethyl benzoate is dissolved in 10 ml of dimethylformamide in a reactor. 0.212 g of thiourea (2 eq.) is subsequently added and the reaction mixture is left to react at reflux (160° C.) for 6 hours.

The reaction mixture is extracted with dichloromethane and then washed with water 3 times. The organic phase is recovered after separating by settling, dried over sodium sulphate, filtered and then concentrated to dryness under vacuum. It is subsequently purified on a column of silica gel (elutent: dichloromethane).

0.12 g of a white powder is obtained (yield: 25%).
$^1$H NMR spectrum (200 MHz; $d_6$-DMSO).

| δ (ppm) | splitting pattern | integration |
| --- | --- | --- |
| 2.95 | s | 6 |
| 6.77 | d | 2 |
| 7.5 | m | 8 |
| 7.7 | d | 2 |
| 8.1 | d | 2 |

EXAMPLE 4

Preparation of 2-phenyl-4,5-di(p-tolyl)oxazole

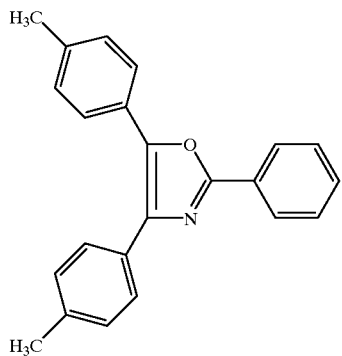

a) Benzoylation: synthesis of 2-oxo-1,2-di(p-tolyl)ethyl benzoate 1 g of dimethylbenzoin with 0.63 g of triethylamine (1.5 eq.) and 0.1 g of dimethylaminopyridine are added to 20 ml of dichloromethane in a reactor with stirring and at 0° C.

0.88 g of benzoyl chloride, in solution in 5 ml of dichloromethane, is gradually introduced using a dropping funnel (the introduction time having a duration of approximately 10 minutes). The reaction mixture is left to react for 5 hours. The reaction mixture is then washed with water three times. The organic phase is recovered after separating by settling, dried over sodium sulphate, filtered and then concentrated to dryness under vacuum. 1.2 g of a white powder are obtained (yield: 84%).

b) Cyclization: synthesis of 2-phenyl-4,5-di(p-tolyl)oxazole 0.5 g of 2-oxo-1,2-di(p-tolyl)ethyl benzoate is dissolved in 10 ml of dimethylformamide in a reactor. 0.22 g of thiourea (2 eq.) is subsequently added and the reaction mixture is left to react at reflux (160° C.) for 5 hours. The solution is poured onto a water/ice mixture. The precipitated product is washed with water, filtered through a sintered glass filter under vacuum and placed overnight in a desiccator before being purified on a column of silica gel with dichloromethane as elutent.

0.27 g of a beige powder is obtained (yield: 60%).

$^1$H NMR spectrum (200 MHz; CDCl$_3$).

| δ (ppm) | splitting pattern | integration |
| --- | --- | --- |
| 2.3 | s | 6 |
| 7.1 | m | 4 |
| 7.5 | m | 7 |
| 8.1 | d | 2 |

EXAMPLE 5

Preparation of 4([8-(4-fluorophenyl)-2-phenyloxazol-4-yl]pyridine

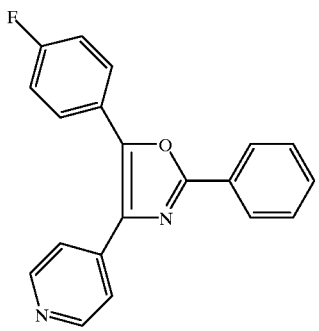

0.72 g of 1-(4-fluorophenyl)-2-oxo-2-(pyridin-4-yl)ethyl benzoate (prepared according to J.O.C., 1984, 27, 72, the disclosure at which is specifically incorporated by reference) is dissolved in 10 ml of dimethylformamide in a reactor. 0.32 g of thiourea (2 eq.) is subsequently added and the reaction mixture is left to react at reflux (160° C.) for 6 hours.

The reaction mixture is extracted with dichloromethane and then washed twice with water, dried over sodium sulphate, filtered and finally brought to dryness under vacuum.

The product obtained is then purified on a silica column (elutent:dichloromethane/methanol:99.5/0.5).

0.18 g of an orange powder is obtained (yield: 27%).

$_1$H NMR spectrum (200 MHz; d$_6$-DMSO).

| δ (ppm) | splitting pattern | integration |
| --- | --- | --- |
| 7.35 | m | 2 |
| 7.6 | m | 5 |
| 7.72 | m | 2 |
| 8.15 | m | 2 |
| 8.64 | m | 2 |

EXAMPLE 6

Preparation of 2-[3-(benzyloxy)propyl]-4,5-diphenyloxazole

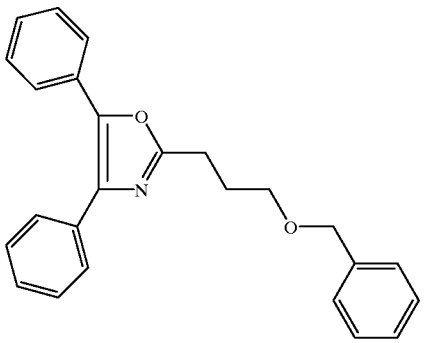

a) Synthesis of 2-oxo-1,2-diphenylethyl 4-(benzyloxy)butanoate 1.5 g of 4-benzyloxybutanoic acid are dissolved in 10 ml of anhydrous toluene in a reactor under a nitrogen atmosphere. 1.45 ml of 98% oxalyl chloride (2.1 eq.) and 4 drops of dimethylformamide, in order to catalyze the reaction, are subsequently added. The reaction mixture is left to react at room temperature for 1 hour. The solution is concentrated to dryness under vacuum. The orange oil obtained is dissolved in dichloromethane and then introduced dropwise into a reactor, placed under a nitrogen atmosphere, comprising a solution of 1.18 g (0.7 eq.) of benzoin and 1.58 g (2 eq.) of triethylamine in dichloromethane. An immediate evolution of gas is recorded. The reaction mixture is left stirring for 3 hours at room temperature. The reaction mixture is washed 3 times with water, dried over anhydrous sodium sulphate, filtered and finally brought to dryness. The esterified product is then isolated on a silica column (elutent:dichloromethane).

0.3 g of a yellow oil is obtained (yield: 60%).

b) Cyclization: synthesis of 2-[3-(benzyloxy)propyl]-4,5-diphenyloxazole 0.3 g of 2-oxo-1,2-diphenylethyl 4-(benzyloxy)butanoate is dissolved in 10 ml of dimethylformamide in a reactor. 0.12 g of thiourea (2 eq.) is subsequently added and the reaction mixture is left to react at reflux (160° C.) for 5 hours. The reaction mixture is extracted with dichloromethane and then washed 3 times with water, dried over sodium sulphate, filtered and finally brought to dryness under vacuum.

The product obtained is then purified on a silica column (elutent:dichloromethane).

0.1 g of a yellow oil is obtained (yield: 35%).

$^1$H NMR spectrum (200 MHz; $d_6$-DMSO).

| δ (ppm)  | splitting pattern | integration |
|----------|-------------------|-------------|
| 2.05     | m                 | 2           |
| 2.9      | t                 | 2           |
| 3.55     | t                 | 2           |
| 4.47     | s                 | 2           |
| 7.3 to 7.6 | m               | 15          |

EXAMPLE 7

Preparation of 2-phenyl-4-(tert-butyl)-5-ethyloxazole

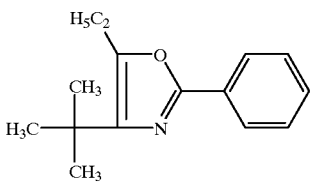

a) Benzoylation: synthesis of 1-ethyl-3,3-dimethyl-2-oxobutyl benzoate 0.31 g of 4-hydroxy-2,2-dimethylhexan-3-one (prepared according to J.O.C., 1991, 56, 3118, the disclosure of which is specifically incorporated by reference) with 0.3 g of triethylamine (1.5 eq.) and a few mg of dimethylaminopyridine (catalyst) are added to a reactor, the mixture being in 5 ml of dichloromethane with stirring and at 0° C.

0.42 g of benzoyl chloride (1.5 eq.), in solution in 5 ml of dichloromethane, is gradually introduced using a dropping funnel (the introduction time having a duration of approximately 10 minutes). The reaction mixture is left stirring for 3 hours at room temperature.

The reaction mixture is washed twice with water and then twice with water saturated with sodium bicarbonate. It is dried over anhydrous sodium sulphate, filtered and finally brought to dryness under vacuum. The benzoylated product is then isolated on a silica column (elutent:dichloromethane).

0.31 g of a yellow oil is obtained (yield: 60%).

b) Cyclization: synthesis of 2-phenyl-4-(tert-butyl)-5-ethyloxazole 0.31 g of 1-ethyl-3,3-dimethyl-2-oxobutyl benzoate is dissolved in 8 ml of dimethylformamide in a reactor. 0.75 g of thiourea (5 eq.) is subsequently added and the reaction mixture is left to react at reflux (160° C.) for 6 hours. The reaction mixture is extracted with dichloromethane and then washed 3 times with water, dried over anhydrous sodium sulphate, filtered and finally brought to dryness under vacuum.

The product obtained is then purified on a silica column (elutent:dichloromethane).

0.1 g of a yellow oil is obtained (yield: 35%).

$^1$H NMR spectrum (200 MHz; $d_6$-DMSO).

| δ (ppm) | splitting pattern | integration |
|---------|-------------------|-------------|
| 1.25    | t                 | 3           |
| 1.35    | s                 | 9           |
| 2.8     | q                 | 2           |
| 7.4     | m                 | 3           |
| 8       | m                 | 2           |

EXAMPLE 8

Preparation of 2,5-diphenyl-4-(tert-butyl)oxazole

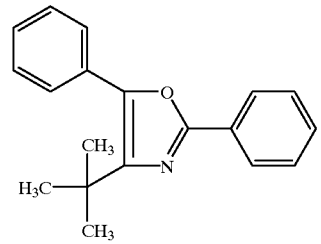

a) Benzoylation: synthesis of 3,3-dimethyl-2-oxo-1-phenylbutyl benzoate 0.45 g of 1-hydroxy-3,3-dimethyl-1-phenylbutan-2-one (prepared according to J.O.C., 1991, 56, 3118, the disclosure of which is specifically incorporated by reference) with 0.3 g of triethylamine (1.5 eq.) and a few mg of dimethylaminopyridine are added to a reactor, the mixture being in 5 ml of dichloromethane with stirring and at 0° C.

0.42 g of benzoyl chloride (1.5 eq.), in solution in 5 ml of dichloromethane, is gradually introduced using a dropping funnel (the introduction time having a duration of approximately 10 minutes). The reaction mixture is left to stir for 3 hours at room temperature. The reaction mixture is washed twice with water and then twice with water saturated with sodium bicarbonate. It is subsequently dried over anhydrous sodium sulphate, filtered and finally brought to dryness under vacuum.

The benzoylated product is then isolated on a silica column (elutent:dichloromethane).

0.40 g of a yellow oil is obtained (yield: 60%).

b) Cyclization: synthesis of 2,5-diphenyl-4-(tert-butyl) oxazole 0.15 g of 3,3-dimethyl-2-oxo-1-phenylbutyl benzoate is dissolved in 8 ml of dimethylformamide in a reactor. 0.2 g of thiourea (5 eq.) is subsequently added and the reaction mixture is left to react at reflux (160° C.) for 15 hours.

The reaction mixture is extracted with dichloromethane and then washed 3 times with water, dried over anhydrous sodium sulphate, filtered and finally brought to dryness under vacuum.

The product obtained is then purified on a silica column (elutent:dichloromethane).

0.06 g of a yellow oil is obtained (yield: 20%).

Mass spectrum: (MH)hu+=m/z =278.

What is claimed is:

1. A process for preparing an oxazole of formula (II):

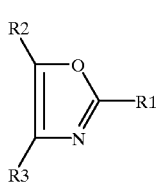

(II)

comprising reacting thiourea with a diketone ester of formula (I):

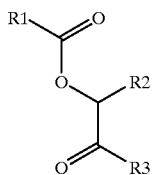

(I)

wherein groups $R_1$, $R_2$, and $R_3$, which are identical or different, are chosen from:
  saturated and unsaturated, linear and branched $C_1$–$C_{12}$ hydrocarbon groups, wherein said $C_1$–$C_{12}$ hydrocarbon groups are unsubstituted or substituted by at least one substituent chosen from —OR, —SR, —NRR', —COOR, —CN, —SO$_n$CH$_3$, —CF$_3$, and halogens;
  aryl groups unsubstituted or substituted by at least one substituent chosen from saturated and unsaturated, linear and branched $C_1$–$C_{12}$ hydrocarbon groups, —OR, —NRR', —COOR, —CN, —SO$_n$CH$_3$, —SR, —CF$_3$ and halogens; and
  saturated and unsaturated $C_{5-10}$ heterocyclic groups comprising at least one heteroatom chosen from N, S, and O, wherein said heterocyclic groups are unsubstituted or substituted by at least one substituent chosen from linear and branched $C_1$–$C_{12}$ hydrocarbon groups, —OR, —NRR', —COOR, —CN, —SO$_n$CH$_3$, —SR, —CF$_3$, and halogens,
wherein R and R', which are identical or different, are each chosen from hydrogen atoms and saturated and unsaturated, linear, branched, and cyclic $C_1$–$C_{12}$ hydrocarbon groups, and n has a value chosen from 0, 1, and 2.

2. The process according to claim 1, wherein said halogens are chosen from clorine and fluorine.

3. The process according to claim 1, wherein said linear, branched, and cyclic $C_1$–$C_{12}$ hydrocarbon groups are chosen from alkyl, aryl, aralkyl, and alkylaryl groups.

4. The process according to claim 1, wherein groups $R_1$, $R_2$ and $R_3$, which are identical or different, are each chosen from:
  saturated, linear and branched $C_1$–$C_6$ hydrocarbon groups;
  saturated, linear and branched, $C_2$–$C_6$ hydrocarbon groups substituted with at least one substituent chosen from —OR, wherein R is chosen from phenyl and alkylaryl groups;
  phenyl groups unsubstituted or substituted by at least one substituent chosen from $C_1$–$C_4$ hydrocarbon groups, —NRR' groups wherein R and R' are chosen from saturated $C_1$–$C_4$ hydrocarbon groups, and halogens; and
  unsaturated $C_5$–$C_6$ heterocyclic groups, comprising a ring having at least one nitrogen atom in the ring.

5. The process according to claim 4, wherein said $C_1$–$C_6$ hydrocarbon groups are chosen from methyl, ethyl, propyl, n-butyl, isobutyl, and tert-butyl groups.

6. The process according to claim 4, wherein said phenyl and alkylaryl groups are chosen from —(CH$_2$)$_n$-phenyl groups, wherein n has a value ranging from 1 to 4.

7. The process according to claim 6, wherein n has a value ranging from 1 to 2.

8. The process according to claim 4, wherein the $C_1$–$C_4$ hydrocarbon groups are chosen from methyl, ethyl, propyl, n-butyl, isobutyl, and tert-butyl groups.

9. The process according to claim 4, wherein said halogen is fluorine.

10. The process according to claim 1, wherein the reaction is carried out in a dipolar aprotic solvent.

11. The process according to claim 1, wherein the reaction is carried out in a dipolar aprotic solvent having a boiling point of greater than 130° C.

12. The process according to claim 1, wherein the reaction is carried out in a dipolar aprotic solvent having a boiling point of greater than 140° C.

13. The process according to claim 1, wherein the reaction is carried out in a dipolar aprotic solvent having a boiling point of greater than 160° C.

14. The process according to claim 1, wherein the reaction is carried out in dimethylformamide.

15. The process according to claim 1, wherein the reaction is carried out at a temperature of at least 130° C.

16. The process according to claim 1, wherein the reaction is carried out at a temperature of at least 140° C.

17. The process according to claim 1, wherein the reaction is carried out at a temperature of at least 160° C.

18. The process according to claim 1, wherein the reaction is carried out in a solvent and at a reflux temperature of the solvent.

19. The process according claim 1, wherein the reaction is carried out under vacuum and in the absence of a solvent, at a temperature close to or greater than a melting point of at least one of said thiourea and diketone ester of formula (I).

20. The process according to claim 1, comprising:
  dissolving the diketone ester of formula (I) and the thiourea in a solvent to form a mixture; and
  heating the mixture to a temperature of at least 130° C. for a time sufficient to bring the reaction to completion.

21. The process according to claim 20, wherein the mixture comprises approximately 1 equivalent of diketone ester of formula (I) for every 2 equivalents of thiourea.

22. The process according to claim 20, wherein the time ranges from approximately 5 to 10 hours.

23. The process according to claim 20, further comprising isolating said oxazole of formula (II).

24. The process according to claim 23, wherein the isolating is accomplished by at least one technique chosen from precipitating, filtrating, and extracting.

25. The process of claim 20, further comprising subjecting the oxazole of formula (II) to at least one process chosen from washing, drying, recrystallizing, and purifying.

* * * * *

UNITED STATES PATENT AND TRADEMARK OFFICE
CERTIFICATE OF CORRECTION

PATENT NO. : 6,333,414 B1
DATED : December 25, 2001
INVENTOR(S) : Maria Dalko et al.

It is certified that error appears in the above-identified patent and that said Letters Patent is hereby corrected as shown below:

<u>Column 11, claim 2,</u>
Line 57, "clorine" should read -- chlorine --.

Signed and Sealed this

Twenty-sixth Day of March, 2002

Attest:

JAMES E. ROGAN
*Attesting Officer*   *Director of the United States Patent and Trademark Office*